United States Patent
Abla et al.

(10) Patent No.: US 10,466,175 B2
(45) Date of Patent: Nov. 5, 2019

(54) CORROSION INHIBITORS AND KINETIC HYDRATE INHIBITORS

(71) Applicant: Ecolab USA Inc., St. Paul, MN (US)

(72) Inventors: Michel Issa Abla, Houston, TX (US); Jeffery Dennis Breshears, Batavia, IL (US); John E. Hoots, Batavia, IL (US); Jeremy Moloney, Katy, TX (US); Allan Scott, Winchester (GB); Peter A. Webber, Sugarland, TX (US)

(73) Assignee: Ecolab USA Inc., St. Paul, MN (US)

( * ) Notice: Subject to any disclaimer, the term of this patent is extended or adjusted under 35 U.S.C. 154(b) by 234 days.

(21) Appl. No.: 15/018,281

(22) Filed: Feb. 8, 2016

(65) Prior Publication Data
US 2016/0231247 A1     Aug. 11, 2016

Related U.S. Application Data

(60) Provisional application No. 62/114,332, filed on Feb. 10, 2015.

(51) Int. Cl.
| | | |
|---|---|---|
| *G01N 21/64* | (2006.01) | |
| *C09K 8/52* | (2006.01) | |
| *C09K 8/54* | (2006.01) | |
| *C09K 8/524* | (2006.01) | |
| *G01N 33/24* | (2006.01) | |

(Continued)

(52) U.S. Cl.
CPC ......... *G01N 21/6428* (2013.01); *G01N 33/24* (2013.01); *C09K 8/52* (2013.01); *C09K 8/524* (2013.01); *C09K 8/54* (2013.01); *G01N 2021/052* (2013.01); *G01N 2021/8416* (2013.01)

(58) Field of Classification Search
CPC ...... G01N 21/6428; C09K 8/52; C09K 8/524; C09K 8/54
See application file for complete search history.

(56) References Cited

U.S. PATENT DOCUMENTS

| | | |
|---|---|---|
| 3,413,227 A | 11/1968 | Howard et al. |
| 4,406,811 A | 9/1983 | Christensen et al. |
| 4,426,208 A | 1/1984 | Perilstein |

(Continued)

FOREIGN PATENT DOCUMENTS

| | | |
|---|---|---|
| EP | 0703451 A2 | 3/1996 |
| WO | WO 2009/155524 A1 | 12/2009 |

OTHER PUBLICATIONS

Durst et al., "Phenacyl Esters of Fatty Acids Via Crown Ether Catalysts for Enhanced Ultraviolet Detection in Liquid Chromatography," *Analytical Chemistry*, 47(11), 1975, pp. 1797-1801.

(Continued)

*Primary Examiner* — Aiqun Li
(74) *Attorney, Agent, or Firm* — Leydig, Voit & Mayer, Ltd.

(57) ABSTRACT

Corrosion inhibitor and kinetic hydrate inhibitor formulations, and methods of using each are provided. Each formulation optionally includes a fluorophore, which can be used to fluorometrically control dosage of each formulation into an aqueous liquid utilized in a downhole application, thereby providing improved precision of dosage into aqueous liquids having relatively high turbidity, and consequently relatively high light absorbance.

17 Claims, 5 Drawing Sheets

(51) Int. Cl.
*G01N 21/05* (2006.01)
*G01N 21/84* (2006.01)

(56) References Cited

U.S. PATENT DOCUMENTS

| | | | |
|---|---|---|---|
| 4,702,574 A * | 10/1987 | Bawa | B29D 11/00317 |
| | | | 264/1.38 |
| 4,783,314 A | 11/1988 | Hoots et al. | |
| 4,964,468 A | 10/1990 | Adams et al. | |
| 4,992,380 A | 2/1991 | Moriarty et al. | |
| 4,994,197 A | 2/1991 | Blain et al. | |
| 5,009,799 A | 4/1991 | Syrinek et al. | |
| 5,171,450 A | 12/1992 | Hoots | |
| 5,225,679 A | 7/1993 | Clarke et al. | |
| 5,278,074 A | 1/1994 | Rao et al. | |
| 5,702,684 A | 12/1997 | McCoy et al. | |
| 5,843,783 A | 12/1998 | Rutledge et al. | |
| 6,107,531 A | 8/2000 | Colle et al. | |
| 6,255,118 B1 | 7/2001 | Alfano et al. | |
| 6,472,219 B1 | 10/2002 | Nieuwenhuis et al. | |
| 6,866,797 B1 | 3/2005 | Martin et al. | |
| 6,966,213 B2 | 11/2005 | Hoots et al. | |
| 6,984,340 B1 | 1/2006 | Brady et al. | |
| 7,057,050 B2 | 6/2006 | Meyer | |
| 7,909,101 B2 | 3/2011 | Conrad | |
| 7,951,754 B2 | 5/2011 | Tiwari et al. | |
| 7,989,403 B2 | 8/2011 | Acosta et al. | |
| 8,105,987 B2 | 1/2012 | Acosta et al. | |
| 8,105,988 B2 | 1/2012 | Acosta et al. | |
| 8,288,323 B2 | 10/2012 | Acosta et al. | |
| 8,329,620 B2 | 12/2012 | Acosta | |
| 8,334,240 B2 | 12/2012 | Acosta | |
| 8,551,925 B2 | 10/2013 | Nguyen et al. | |
| 8,585,930 B2 | 11/2013 | Tiwari | |
| 8,618,025 B2 | 12/2013 | Webber | |
| 8,618,027 B2 | 12/2013 | Meyer et al. | |
| 8,911,615 B2 | 12/2014 | Raney et al. | |
| 8,921,478 B2 | 12/2014 | Conrad et al. | |
| 2001/0029701 A1 | 10/2001 | Ahern et al. | |
| 2003/0006385 A1 | 1/2003 | Banks | |
| 2004/0157334 A1 | 8/2004 | Barashkov et al. | |
| 2005/0008532 A1 | 1/2005 | Jenkins et al. | |
| 2005/0025660 A1 | 2/2005 | Hoots et al. | |
| 2006/0214112 A1 | 9/2006 | Resch-Genger et al. | |
| 2009/0260454 A1 | 10/2009 | Young et al. | |
| 2009/0319195 A1 | 12/2009 | Hoots et al. | |
| 2010/0099807 A1 * | 4/2010 | Carlise | C10L 3/003 |
| | | | 524/377 |
| 2010/0099814 A1 | 4/2010 | Conrad et al. | |
| 2015/0034319 A1 | 2/2015 | Taylor | |

OTHER PUBLICATIONS

Erwin, "Symposium on Processing and Product Selectivity of Synthetic Fuels," American Chemical Society, Aug. 1992, pp. 1915-1923.

Gieleciak et al., "Detailed hydrocarbon analysis of FACE diesel fuels using comprehensive two-dimensional gas chromatography," Technical Report of Natural Resource Canada, Report CDEV-2013-2065-RT, Oct. 2013, 95 pp.

International Fuel Quality Center, "Setting a Quality Standard for Fuel Ethanol," 2004, International Fuel Quality Center, Hart Downstream Energy Services, pp. 1-56.

Thomas et al., "Analysis of Commercial Diesel Fuels by Preparative High Performance Liquid Chromatography and Gas Chromatography-Mass Spectrometry," *ACS Fuels Volumes FALL (Chicago)*, 1985, 30(4), pp. 76-84.

Wilde et al., "Techniques of Water-Resources Investigations of the United States Geological Survey, Book 9," U.S. Geological Survey, 1998-, pp. 18-28.

Israel Patent Office, International Search Report in International Patent Application No. PCT/US2016/016999, dated May 24, 2016, 4 pp.

Israel Patent Office, Written Opinion in International Patent Application No. PCT/US2016/016999, dated May 24, 2016, 6 pp.

Schnegg et al., "Sonde for Downhole Measurement of Water Turbidity and Dye Tracer Concentration," in *Articles of Geomagnetism Group*, University of Neuchâtel, Swets & Zeitlinger, Lisse, The Netherlands, 2001, pp. 795-798.

European Patent Office, Extended European Search Report in European Patent Application No. 16749664.5, 8 pp. (dated Nov. 19, 2018).

* cited by examiner

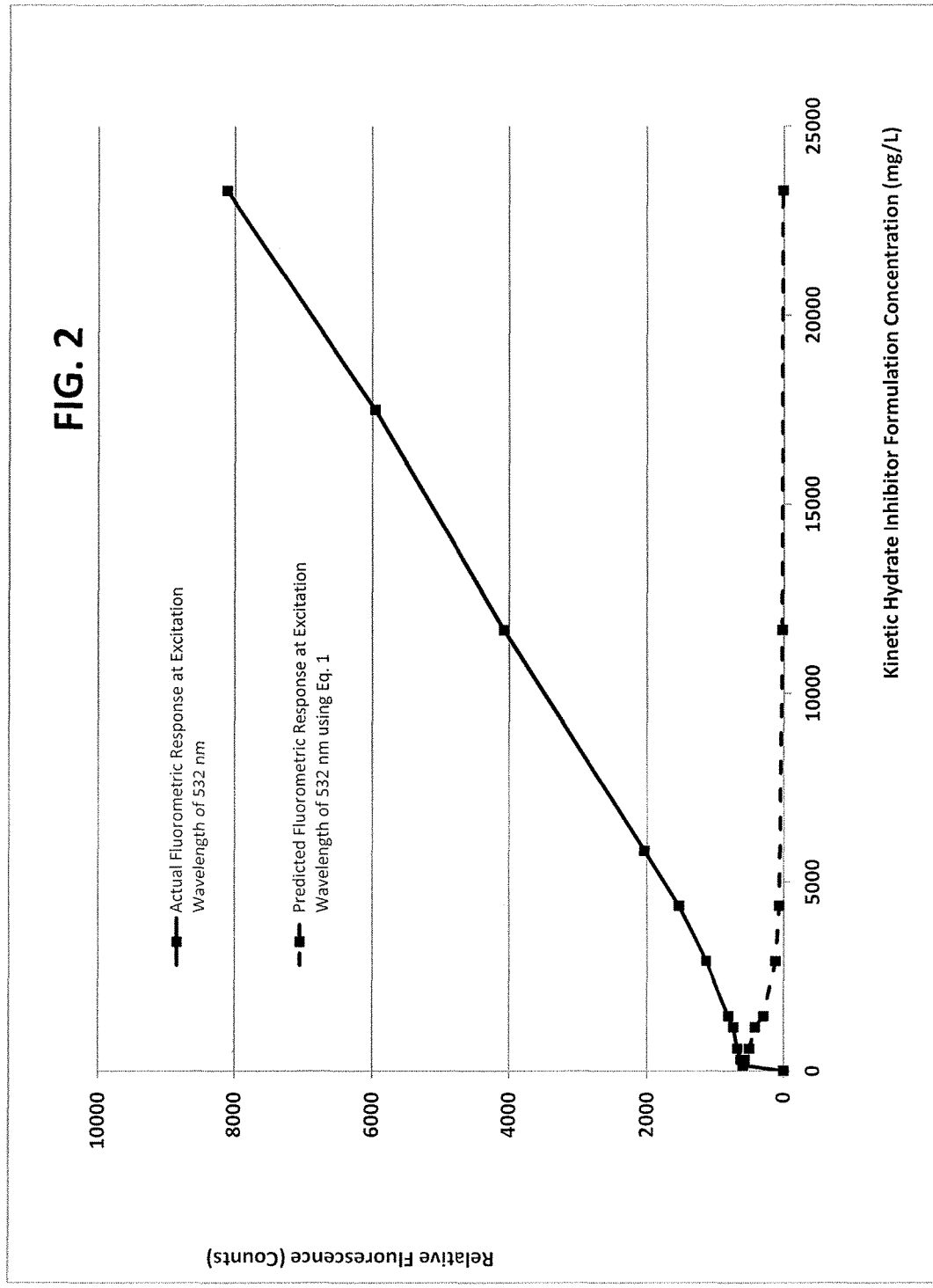

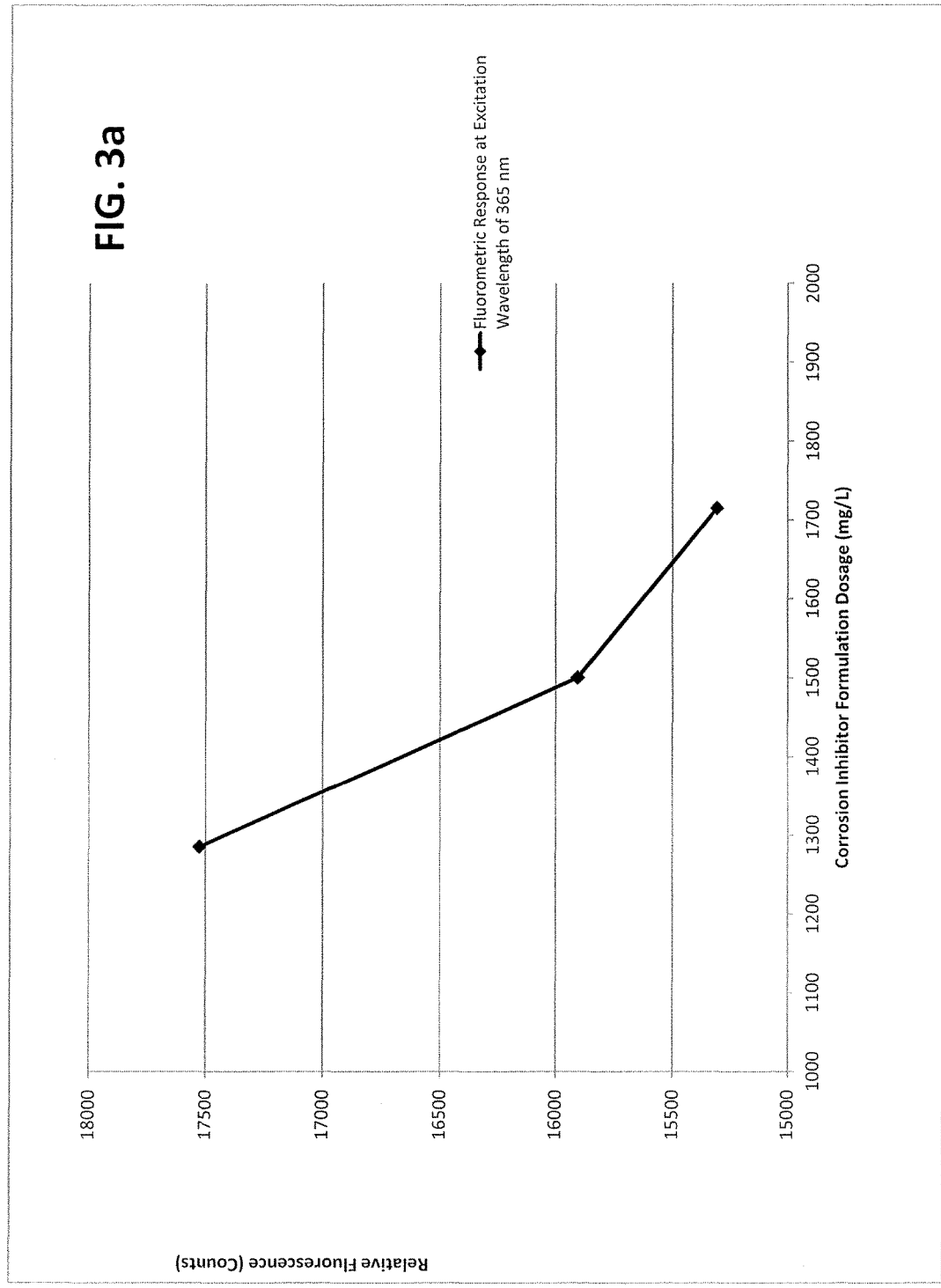

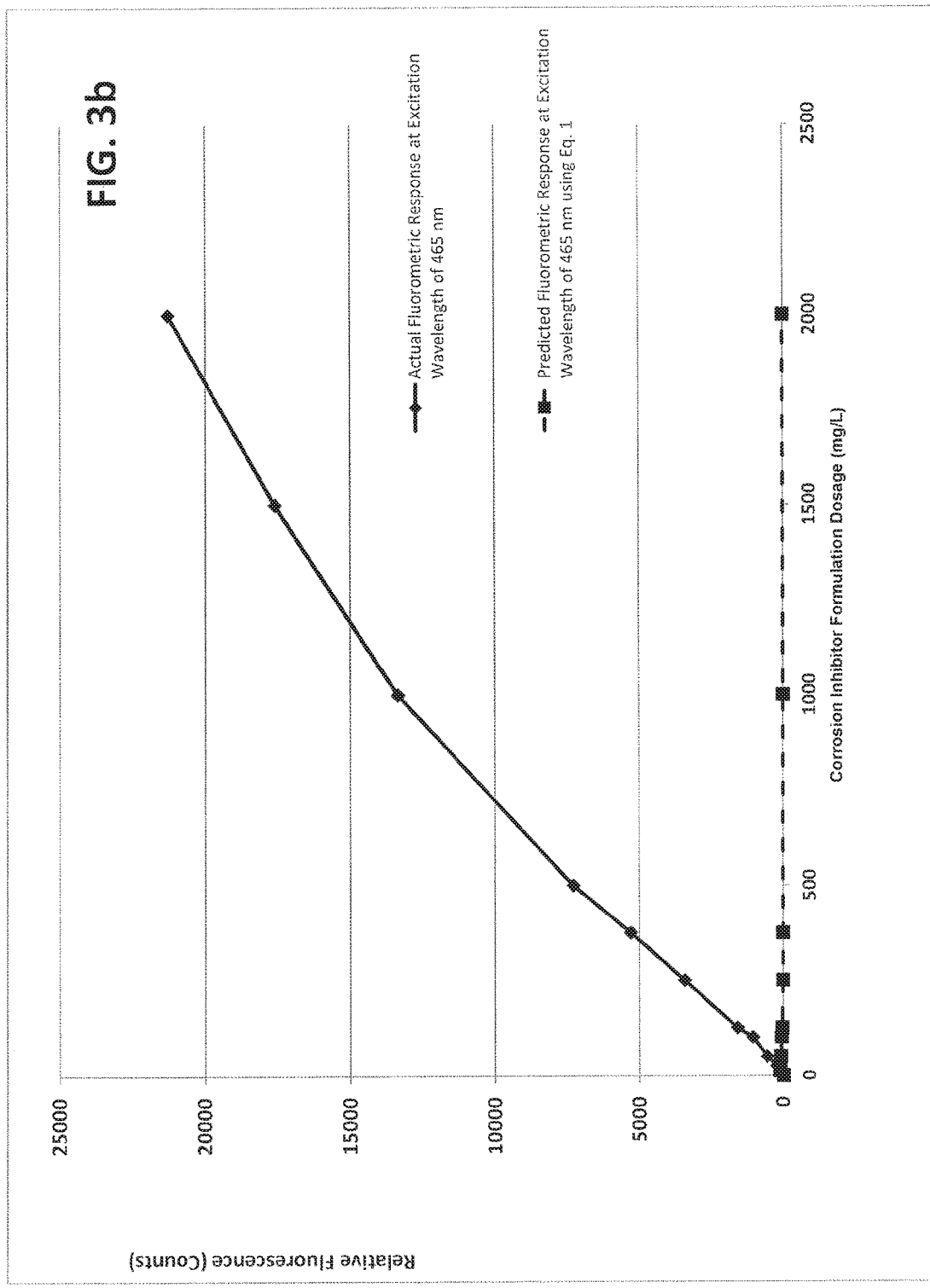

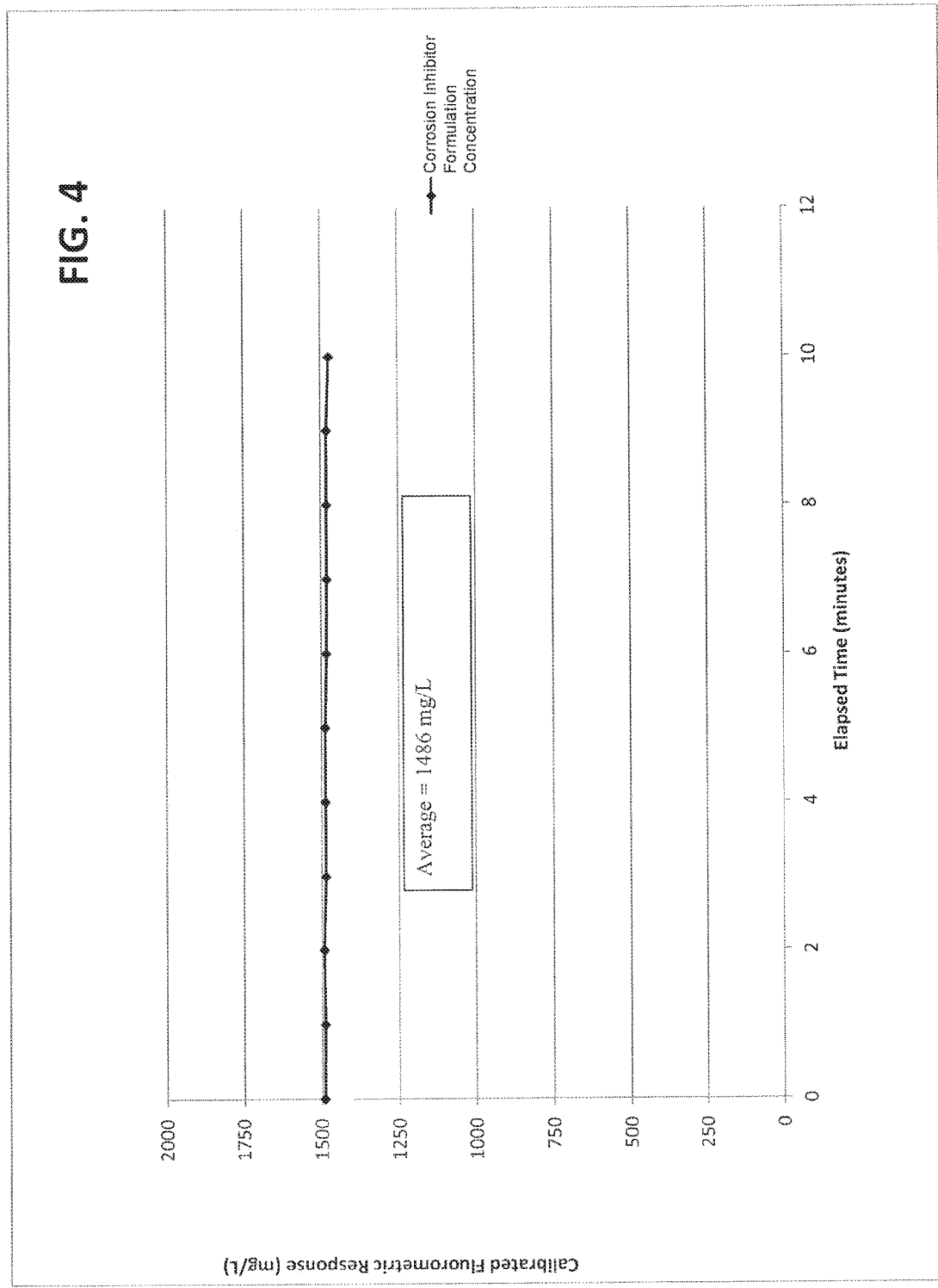

CORROSION INHIBITORS AND KINETIC HYDRATE INHIBITORS

This application claims the benefit of U.S. Provisional Patent Application Ser. No. 62/114,332, filed Feb. 10, 2015, the disclosure of which is incorporated herein by reference in its entirety.

BACKGROUND

Use of fluorescence techniques often involves a direct correlation between a fluorophore concentration and fluorometric response (i.e., as the fluorophore concentration increases, so does the fluorometric response). When measuring fluorescence in liquid solutions (e.g., aqueous liquids), relatively high light absorbance and/or turbidity of the liquid solution can prevent obtaining a direct correlation as set forth above, thereby complicating or altogether preventing the use of traditional fluorometric techniques to measure fluorometric response in practical applications. Particularly in cases of relatively high levels of light absorbance from a fluorophore (e.g., greater than about 0.4 absorbance units combined total for excitation and emission lightpaths when using a 1 cm pathlength cell), fluorometric response can even decrease as fluorophore concentration increases, which can occur whether the fluorophore is the only source of light absorbance or whether overall light absorbance is due to the fluorophore and other substances present in the relevant sample. A decrease in fluorometric response as fluorophore concentration increases is an undesirable result for practical applications.

The impact of light absorbance on fluorometric intensity (an example of a fluorometric response) can be predicted using Equation 1 below:

$$\text{\% total fluorometric intensity} = [(10^{-0.5*L1*Aex})*100] * [(10^{-0.5*L2*Aem})*100] \quad \text{Eq. 1}$$

wherein L1=the width across a sample chamber (e.g., a cylindrical flow cell) in the direction that the light is being shone; L2=the width across the sample chamber in the direction of fluorometric response toward a fluorometric detector; Aex=light absorbance at 1 cm of pathlength of a sample at an excitation wavelength(s); and Aem=light absorbance at 1 cm of pathlength of a sample at an emission wavelength(s). Equation 1 assumes that the fluorometric response originates at the center of the sample chamber.

Generally, aqueous liquids utilized in downhole applications are treated with any of several treatment formulations. Aqueous liquids utilized in downhole applications are generally relatively turbid (e.g., from about 100 NTU to about 130,000 NTU) and have relatively high light absorbance, making them less than ideal candidates for fluorometrically measuring the concentrations of certain compositions present therein. Historically, such treatment formulations (e.g., corrosion inhibitor formulation and/or kinetic hydrate inhibitor formulation) have been difficult if not impossible to measure their concentrations and/or control their dosages via traditional fluorometric techniques.

SUMMARY

Corrosion inhibitor formulations are provided. In an embodiment, the corrosion inhibitor formulation comprises an alkyl pyridine quaternary ammonium salt, a phosphate ester, an ethoxylated fatty amine, an imidazoline, a benzyl alkyl pyridinium salt, and an organic solvent.

Kinetic hydrate inhibitor formulations are provided. The kinetic hydrate inhibitor formulation comprises an organic solvent, an alkyl substituted polyamide homopolymer, an alkyl substituted polyamide copolymer, and optionally a fluorophore.

Methods of treating an aqueous liquid utilized in a downhole application are provided. In an embodiment, the method comprises dosing a kinetic hydrate inhibitor formulation at a kinetic hydrate inhibitor dosage rate into the aqueous liquid utilized in the downhole application. The aqueous liquid comprises water, a surfactant (e.g., an ethoxylated fatty amine), an organic solvent, and at least one of an alkyl pyridine quaternary ammonium salt and a phosphate ester. The kinetic hydrate inhibitor formulation comprises an alkyl substituted polyamide homopolymer and an alkyl substituted polyamide copolymer.

In an embodiment, the method of treating an aqueous liquid utilized in a downhole application comprises dosing a corrosion inhibitor formulation at a corrosion inhibitor dosage rate into the aqueous liquid utilized in the downhole application. The corrosion inhibitor formulation comprises an active ingredient and an organic solvent, the corrosion inhibitor formulation being capable of providing a fluorometric response proportional to the concentration of the dosed corrosion inhibitor formulation, or active ingredient thereof, when present in the aqueous liquid utilized in the downhole application. A fluorometric response proportional to the concentration of the dosed corrosion inhibitor formulation, or active ingredient thereof, present in the aqueous liquid containing the dosed corrosion inhibitor formulation is created and measured. The corrosion inhibitor dosage rate into the aqueous liquid is adjusted based on the created and measured fluorometric response. The method may further comprise dosing a kinetic hydrate inhibitor formulation at a kinetic hydrate inhibitor dosage rate into the aqueous liquid utilized in the downhole application.

In an embodiment, the method of treating an aqueous liquid utilized in a downhole application comprises dosing a corrosion inhibitor formulation at a corrosion inhibitor dosage rate into the aqueous liquid utilized in the downhole application. A kinetic hydrate inhibitor formulation is dosed into the aqueous liquid utilized in the downhole application at a kinetic hydrate inhibitor dosage rate. The kinetic hydrate inhibitor formulation comprises an active ingredient, an organic solvent, and a tracer at a known ratio with the active ingredient and capable of providing a fluorometric response proportional to the concentration of the dosed kinetic hydrate inhibitor formulation, or active ingredient thereof, when present in the aqueous liquid utilized in the downhole application. A fluorometric response proportional to the concentration of the dosed kinetic hydrate inhibitor formulation, or active ingredient thereof, present in the aqueous liquid containing the dosed corrosion inhibitor and kinetic hydrate inhibitor formulations is created and measured. The kinetic hydrate inhibitor dosage rate is adjusted based on the created and measured fluorometric response.

A method of controlling dosage of corrosion inhibitor into an aqueous liquid utilized in a downhole application is provided. The method comprises dosing a corrosion inhibitor formulation at a corrosion inhibitor dosage rate into the aqueous liquid utilized in the downhole application. The corrosion inhibitor formulation comprises an active ingredient and an organic solvent. The corrosion inhibitor formulation is capable of providing a fluorometric response proportional to the concentration of the dosed corrosion inhibitor formulation, or active ingredient thereof, when present in the aqueous liquid utilized in the downhole application. Light having a wavelength of from about 210 nm to about 830 nm is shone into the aqueous liquid containing the corrosion inhibitor formulation, thereby causing a fluorometric emission at a wavelength of from about 230 nm to about 850 nm. The fluorometric emission at the wavelength of from about 230 nm to about 850 nm is detected. The corrosion inhibitor dosage rate into the aqueous liquid is adjusted based on the detected fluorometric emission at the wavelength of from about 230 nm to about 850 nm.

A method of controlling dosage of kinetic hydrate inhibitor into an aqueous liquid utilized in a downhole application is provided. The method comprises dosing a corrosion inhibitor formulation at a corrosion inhibitor dosage rate into the aqueous liquid utilized in the downhole application. A kinetic hydrate inhibitor formulation is dosed at a kinetic hydrate inhibitor dosage rate into the aqueous liquid utilized in the downhole application. The kinetic hydrate inhibitor formulation comprises an active ingredient, an organic solvent, and a tracer at a known proportion with the active ingredient. The kinetic hydrate inhibitor formulation is capable of providing a fluorometric response proportional to the concentration of the dosed kinetic hydrate inhibitor formulation, or active ingredient thereof, when present in the aqueous liquid utilized in the downhole application. Light having a wavelength of from about 210 nm to about 830 nm is shone into the aqueous liquid containing the corrosion inhibitor and kinetic hydrate inhibitor formulations, thereby causing a fluorometric emission at a wavelength of from about 230 nm to about 850 nm. The fluorometric emission at the wavelength of from about 230 nm to about 850 nm is detected. The kinetic hydrate inhibitor dosage rate into the aqueous liquid is adjusted based on the detected fluorometric emission at the wavelength of from about 230 nm to about 850 nm.

BRIEF DESCRIPTION OF THE SEVERAL VIEWS OF THE DRAWINGS

FIG. 2 is a plot of experimental data collected in Example 2;

FIG. 3a is a plot of experimental data collected in Example 3 related to actual fluorometric response of a corrosion inhibitor formulation present in an aqueous liquid utilized in a downhole application at an excitation wavelength of 365 nm;

FIG. 3b is a plot of experimental data collected in Example 3 related to predicted and actual fluorometric response of a corrosion inhibitor formulation present in an aqueous liquid utilized in a downhole application at an excitation wavelength of 465 nm; and FIG. 4 is a plot of experimental data collected in Example 4.

DETAILED DESCRIPTION

Figure 1:
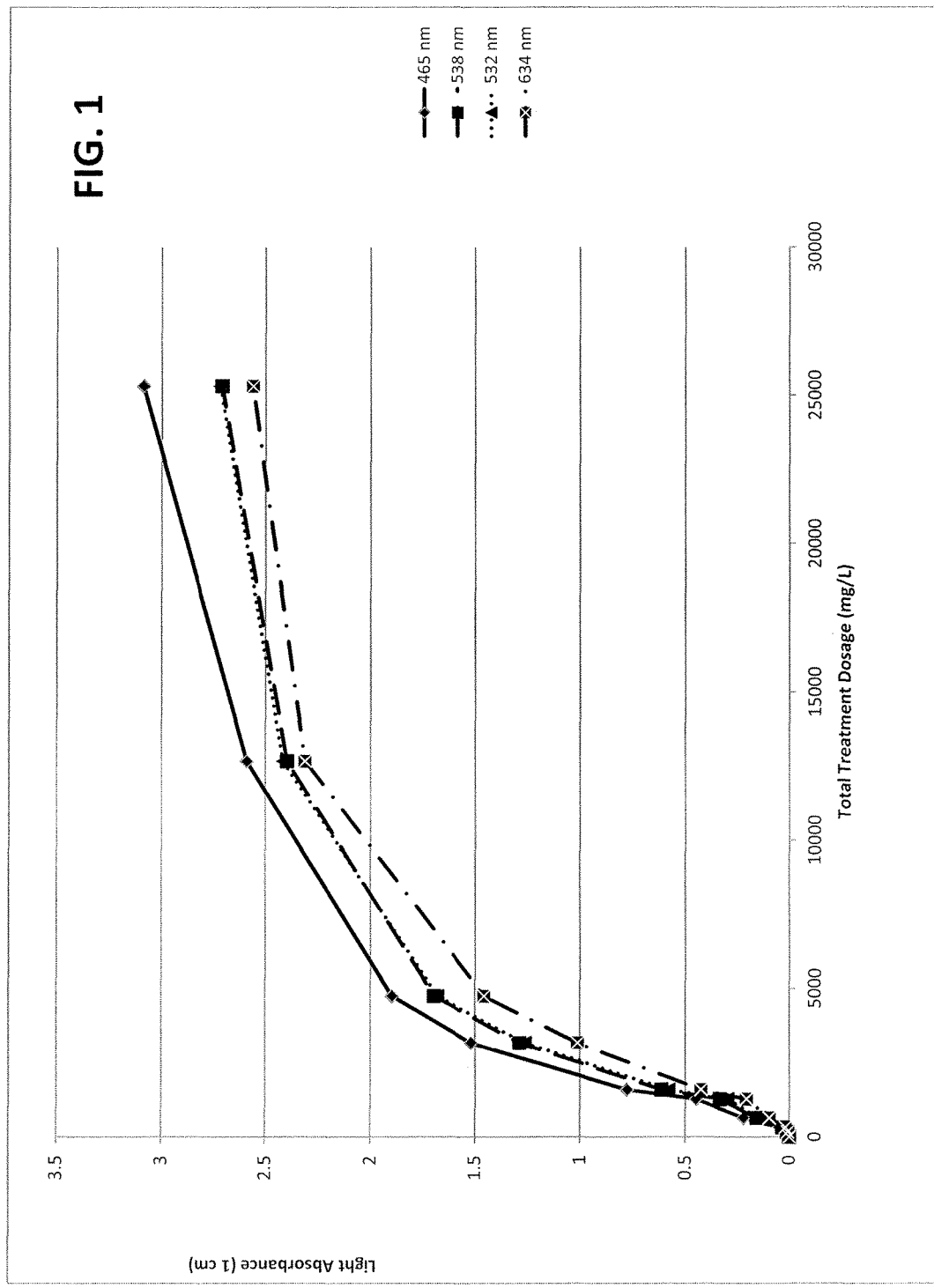
FIG. 1 is a plot of experimental data collected in Example 1.

Formulations and methods are provided that can be used to treat aqueous liquids. More particularly, formulations and methods are provided that can be used in the treatment of aqueous liquids utilized in downhole applications, e.g., wells used for extracting subterranean fluid hydrocarbon substances. The formulations and methods provided herein are particularly useful in the treatment of aqueous liquids utilized in downhole applications where the subterranean fluid hydrocarbon substances being extracted are gaseous. Furthermore, certain embodiments of the methods provided herein relate to controlling dosage of corrosion inhibitor and/or kinetic hydrate inhibitor into an aqueous liquid utilized in a downhole application.

Corrosion inhibitor formulations are provided. In an embodiment, the corrosion inhibitor formulation comprises an alkyl pyridine quaternary ammonium salt, a phosphate ester, an ethoxylated fatty amine, an imidazoline, a benzyl alkyl pyridinium salt, and an organic solvent.

In certain embodiments, the corrosion inhibitor formulation comprises an alkyl pyridine quaternary ammonium salt, which may be an alkyl pyridine quaternary ammonium chloride. The alkyl chain of the alkyl pyridine quaternary ammonium salt may be from $C_1$ to $C_4$, and combinations thereof, such as methyl pyridine quaternary ammonium salt, ethyl pyridine quaternary ammonium salt, propyl pyridine quaternary ammonium salt, butyl pyridine quaternary ammonium salt, and combinations thereof. In a preferred embodiment, the alkyl chain of the alkyl pyridine quaternary ammonium salt may be from $C_1$ to $C_2$, and combinations thereof, such as methyl pyridine quaternary ammonium salt, ethyl pyridine quaternary ammonium salt, and combinations thereof.

The alkyl pyridine quaternary ammonium salt may be present in the corrosion inhibitor formulation at a concentration of from about 15 weight percent to about 35 weight percent, including from about 15 weight percent, or from about 20 weight percent, or from about 22 weight percent, to about 35 weight percent, or to about 30 weight percent, or to about 28 weight percent. In a preferred embodiment, the alkyl pyridine quaternary ammonium salt is present in the corrosion inhibitor formulation at a concentration of from about 22 weight percent to about 28 weight percent, including at a concentration of about 25 weight percent.

The phrase "at a concentration of . . . weight percent" is recited herein and describes various concentrations (e.g., weight percents), or ranges thereof, generally of components of one of the corrosion inhibitor formulations or kinetic hydrate inhibitor formulations disclosed herein. Unless clearly indicated otherwise, such weight percent values are based on the formulation as a whole. For example, the previous paragraph refers to a preferred embodiment of the corrosion inhibitor formulation. In the exemplary preferred embodiment, the alkyl pyridine quaternary ammonium salt is present in the corrosion inhibitor formulation at a concentration of about 25 weight percent, which refers to about 25 weight percent of the corrosion inhibitor formulation as a whole.

In certain embodiments, the corrosion inhibitor formulation comprises a phosphate ester (i.e., an organophosphate, or an ester of phosphoric acid), which in certain embodiments is a mono phosphate ester, a bis phosphate ester, and combinations thereof, and any of which may or may not be oxalated.

The phosphate ester may be present in the corrosion inhibitor formulation at a concentration of from about 5 weight percent to about 20 weight percent, including from about 5 weight percent, or from about 7 weight percent, or from about 9 weight percent, or from about 11 weight percent, or from about 12 weight percent, to about 20 weight percent, or from about 18 weight percent, or from about 16 weight percent, or from about 14 weight percent, or to about 13 weight percent. In a preferred embodiment, the phosphate ester is present in the corrosion inhibitor at a concentration of from about 12 weight percent to about 13 weight percent, including at a concentration of about 12.5 weight percent.

In certain embodiments, the alkyl pyridine quaternary ammonium salt and the phosphate ester are present in the corrosion inhibitor formulation at a known weight ratio. In certain embodiments, the alkyl pyridine quaternary ammonium salt and the phosphate ester are present in the corrosion inhibitor formulation at an alkyl pyridine quaternary ammonium salt-to-phosphate ester weight ratio of from about 1:1 to about 5:1. In a preferred embodiment, the alkyl pyridine quaternary ammonium salt and the phosphate ester are present in the corrosion inhibitor formulation at an alkyl pyridine quaternary ammonium salt-to-phosphate ester weight ratio of about 2:1.

In certain embodiments, the corrosion inhibitor formulation comprises an ethoxylated fatty amine. Exemplary embodiments of ethoxylated fatty amines include, but are not limited to, an ethoxylated tallow amine, ethoxylated coco amine, and combinations thereof. In a preferred embodiment, the corrosion inhibitor formulation comprises an ethoxylated tallow amine.

The ethoxylated fatty amine may be present in the corrosion inhibitor formulation at a concentration of from about 0.1 weight percent to about 10 weight percent, including from about 0.1 weight percent, or from about 1 weight percent, or from about 2 weight percent, or from about 3 weight percent, to about 10 weight percent, or to about 8 weight percent, or to about 6 weight percent, or to about 4 weight percent. In a preferred embodiment, the ethoxylated fatty amine is present in the corrosion inhibitor formulation at a concentration of from about 3 weight percent to about 4 weight percent, including about 3.5 weight percent.

In certain embodiments, the corrosion inhibitor formulation comprises an imidazoline, which includes, but is not limited to, an imidazolinium salt. Exemplary embodiments of imidazolines and imidazolinium salts include, but are not limited to, those disclosed in U.S. Pat. Nos. 7,057,050; 7,951,754; and 8,551,925, each disclosure of which is incorporated herein by reference in its entirety. In a preferred embodiment, the imidazoline is a benzyl imidazolinium salt, which is more preferably benzyl imidazolinium chloride.

The imidazoline may be present in the corrosion inhibitor formulation at a concentration of from about 0.1 weight percent to about 10 weight percent, including from about 0.1 weight percent, or from about 1 weight percent, or from about 2 weight percent, or from about 3 weight percent, to about 10 weight percent, or to about 8 weight percent, or to about 6 weight percent, or to about 4 weight percent. In a preferred embodiment, the imidazoline is present in the corrosion inhibitor formulation at a concentration of from about 3 weight percent to about 4 weight percent, including about 3.5 weight percent.

In certain embodiments, the corrosion inhibitor formulation comprises a benzyl alkyl pyridinium salt (i.e., benzyl alkyl pyridine salt). In a preferred embodiment, the benzyl alkyl pyridinium salt is a benzyl alkyl pyridinium chloride.

The benzyl alkyl pyridinium salt may be present in the corrosion inhibitor formulation at a concentration of from about 0.1 weight percent to about 10 weight percent, including from about 0.1 weight percent, or from about 1 weight percent, or from about 2 weight percent, or from about 3 weight percent, to about 10 weight percent, or to about 8 weight percent, or to about 6 weight percent, or to about 4 weight percent. In a preferred embodiment, the benzyl alkyl pyridinium salt is present in the corrosion inhibitor formulation at a concentration of from about 3 weight percent to about 4 weight percent, including about 3.5 weight percent.

In certain embodiments, the corrosion inhibitor formulation comprises an organic solvent. In certain embodiments, the organic solvent comprises at least one compound selected from an alkyl benzene, a dialkyl benzene, an indate, a tetralin, an indene, naphthalene, alkylnaphthalene, biphenyl, acenpthene, acenaphthylene, alkyldibenzothiophene, alkyldibenzofuran, alkylcarbazole, alkylanthracene, alkylphenanthrene, derivatives thereof, and combinations thereof.

In certain embodiments, the organic solvent comprises at least one compound selected from a mono-ring aromatic compound, a di-ring aromatic compound, a tri-ring aromatic compound, and combinations thereof, each of which is capable of producing a fluorometric response at an excitation wavelength of from about 210 nm to about 830 nm. In certain embodiments, the organic solvent may further comprise a 4-ring aromatic, a 5-ring aromatic, or combinations thereof. In certain embodiments, the organic solvent comprises a component selected from diesel fuel, gasoline, jet fuel, kerosene, fuel oil, and bunker fuel. In preferred embodiments, the organic solvent comprises, consists essentially of, or consists of diesel fuel, which in a particularly preferred embodiment is #2 diesel fuel. Diesel fuel comprises combinations of mono-ring aromatic compounds, di-ring aromatic compounds, and tri-ring aromatic compounds.

The organic solvent is present in the corrosion inhibitor formulation at a concentration of from about 5 weight percent to about 20 weight percent, including from about 5 weight percent, or from about 7 weight percent, or from about 9 weight percent, or from about 11 weight percent, or from about 12 weight percent, to about 20 weight percent, or from about 18 weight percent, or from about 16 weight percent, or from about 14 weight percent, or to about 13 weight percent. In a preferred embodiment, the organic solvent is present in the corrosion inhibitor at a concentration of from about 12 weight percent to about 13 weight percent, including at a concentration of about 12.5 weight percent. In certain embodiments, the organic solvent is present in the corrosion inhibitor formulation at a known ratio to at least one active ingredient of the corrosion inhibitor formulation, as further described herein.

Generally, the corrosion inhibitor formulation is formulated with the intent of being dosed into an aqueous liquid utilized in a downhole application as a dispersion. For example, because of the organic solvent, the corrosion inhibitor formulation is generally dispersed into the aqueous liquid, i.e., dosed as an organic dispersion into the aqueous liquid. Ideally, the organic solvent will allow the more hydrophobic components (e.g., the relatively long chain organic components) of the corrosion inhibitor formulation to become dissolved in the organic phase and interact with the surfactants of the corrosion inhibitor formulation, thereby allowing for dispersion into the aqueous liquid. In a preferred embodiment, diesel fuel allows hydrophobic components of the corrosion inhibitor to become dissolved and interact with surfactants of the corrosion inhibitor. This interaction allows for the corrosion inhibitor formulation to disperse in the aqueous liquid instead of forming a sticky deposit on metallic surfaces of the downhole application, thereby allowing for better corrosion inhibition than in the absence of the organic solvent, e.g., diesel fuel. Without the organic solvent, the corrosion inhibitor formulation would have a tendency to form a sticky deposit in the downhole application, leading to flow assurance and integrity issues in the downhole application.

Several salt compositions are disclosed herein, e.g., alkyl pyridine quaternary ammonium salt, benzyl imidazolinium salt, benzyl alkyl pyridinium salt, etc. Exemplary embodiments of each salt composition is the chloride, e.g., alkyl pyridine quaternary ammonium chloride, benzyl imidazolinium chloride, benzyl alkyl pyridinium chloride, etc., though other salts are contemplated, e.g., sulfates, bromides, and the like.

In certain embodiments, the corrosion inhibitor formulation is capable of producing a fluorometric response proportional to the concentration of the corrosion inhibitor formulation, or active ingredient thereof, when present in an aqueous liquid. In certain embodiments, the corrosion inhibitor formulation is capable of producing a fluorometric response proportional to at least one of the alkyl pyridine quaternary ammonium salt and the phosphate ester present in an aqueous liquid. In certain embodiments, the fluorometric response is capable of being produced by light shone into the aqueous liquid at an excitation wavelength of from about 210 nm to about 830 nm, including from about 210 nm, or from about 350 nm, or from about 440 nm, to about 830 nm, or to about 680 nm, or to about 600 nm, or to about 520 nm. In a preferred embodiment, the fluorometric response is capable of being produced by light shone into the aqueous liquid at an excitation wavelength of from about 440 nm to about 520 nm.

In a preferred embodiment, the corrosion inhibitor formulation is capable of producing a fluorometric response proportional to the concentration of the corrosion inhibitor formulation, or active ingredient thereof, when present in an aqueous liquid having a turbidity of from about 0 NTU to about 130,000 NTU and/or in the absence of extracted liquid hydrocarbon substances, e.g., liquid fossil fuels. In certain embodiments, the corrosion inhibitor formulation is capable of producing a fluorometric response proportional to at least one of the alkyl pyridine quaternary ammonium salt and the phosphate ester when present in an aqueous liquid having a turbidity of from about 0 NTU to about 130,000 NTU and/or in the absence of extracted liquid hydrocarbon substances, e.g., liquid fossil fuels. Generally, aqueous liquids utilized in downhole applications are relatively turbid, i.e., have turbidities of from about 100 NTU to about 130,000 NTU, and the formulations and methods disclosed herein are capable of being used in even such generally turbid aqueous liquids.

The phrase "proportional to the concentration of" is used at various places herein to describe the ability of a fluorometric response to provide information related to the concentration of a particular chemical species present in a substance. For example, if a chemical species was present at a relatively large concentration, then the proportional fluorometric response would be a fluorometric emission of a relatively large intensity, compared to when the chemical species is present in a relatively small concentration. The fluorometric response may, in certain circumstances, be calibrated to particular concentrations (e.g., parts per million of the chemical species per fluorometric units), or the raw fluorometric response may be used to provide information (e.g., feedback control) related to the dosage or control of the dosage into the substance (e.g., an aqueous liquid utilized in a downhole application).

When present, the capability of producing a fluorometric response is caused by the presence of a fluorophore in the corrosion inhibitor formulation. The fluorophore may be present in any one or more of several different chemical forms, including but not limited to one or more compositions that provide function to the corrosion inhibitor formulation (i.e., one or more components, or parts thereof, of the corrosion inhibitor formulation) and one or more compositions that do not provide function to the corrosion inhibitor formulation (i.e., one or more tracers).

For example, tracers that may be present in the corrosion inhibitor formulation include, but are not limited to, one or more aromatic fluorophores, one or more of certain rare earth ions, and/or one or more of certain small molecules capable of producing a fluorometric response. In certain embodiments, the fluorophore is an aromatic fluorophore, which may include, but is not limited to, a dye or intermediate thereof, present in the corrosion inhibitor formulation. In certain embodiments, the fluorophore is a rare earth ion present in the corrosion inhibitor formulation. In certain embodiments, the fluorophore is a small molecule fluorescent compound present in the corrosion inhibitor formulation. When utilized, a tracer is generally present in the corrosion inhibitor formulation at relatively low concentrations, e.g., from about 0.0000001 weight percent to about 1 weight percent, or from about 0.00001 weight percent to about 1 weight percent. In certain embodiments, the tracer is an inert fluorescent tracer. The term "inert," as it pertains to fluorescent tracers, refers to fluorescent tracers that are not appreciably or significantly affected by any other chemistry that the fluorescent tracer(s) may contact while carrying out the methods described herein. For example, inert fluorescent tracers are described in U.S. Pat. No. 6,472,219, which is incorporated herein by reference in its entirety.

In certain embodiments, the fluorophore is a component, or part thereof, present in the corrosion inhibitor formulation. For example, diesel fuel generally comprises several aromatic fluorophores that are capable of producing a fluorometric response at an excitation wavelength of from about 210 nm to about 830 nm, including from about 350 nm, or from about 440, to about 600 nm, or to about 520 nm. When utilized as an organic solvent of a corrosion inhibitor formulation, diesel fuel is a component of the corrosion inhibitor formulation, and the several aromatic fluorophores are "parts thereof." The presence of the aromatic fluorophores in diesel fuel, and consequently in corrosion inhibitor formulations that utilize diesel fuel, allows for the ability to fluorometrically detect the presence of one or more of the aromatic fluorophores, e.g., when dosed as part of a corrosion inhibitor formulation into an aqueous liquid utilized in a downhole application.

In certain embodiments, the corrosion inhibitor formulation further comprises one or more of several components, for example, an ethoxyalcohol (e.g., ethoxybutanol), a polyol (e.g., ethylene glycol, propylene glycol, glycerin, triethylene glycol, and combinations thereof), and 2-mercaptoethanol. Additional examples of ethoxyalcohols, polyols, and 2-mercaptoethanol suitable for use in corrosion inhibitor formulations are further described in U.S. Pat. Nos. 4,964,468; 6,866,797; 7,057,050; 7,951,754; 8,551,925; 8,585,930; and 8,618,027.

Kinetic hydrate inhibitor formulations are provided. In an embodiment, the kinetic hydrate inhibitor formulation comprises an organic solvent, an alkyl substituted polyamide homopolymer, and an alkyl substituted polyamide copolymer. In certain embodiments, the kinetic hydrate inhibitor formulation is capable of producing a fluorometric response at an excitation wavelength of from about 210 nm to about 830 nm. In certain embodiments, the kinetic hydrate inhibitor formulation further comprises a tracer as described herein. In certain embodiments, the kinetic hydrate inhibitor formulation is capable of utilization as a kinetic hydrate inhibitor in an aqueous liquid in a downhole application at temperatures of from about 0° C. to about 100° C. Additional examples of kinetic hydrate inhibitor formulations can be found in U.S. Pat. Nos. 6,107,531; 8,288,323; 8,329,620; 8,334,240; 8,618,025; and 8,921,478, and U.S. Patent Application Publication No. 2010/0099807, each of which is incorporated herein by reference in its entirety.

In certain embodiments, the kinetic hydrate inhibitor comprises an organic solvent as described herein. Further or in the alternative, the organic solvent of the kinetic hydrate inhibitor may comprise a compound selected from a heavy aromatic naphtha, naphthalene, ethylbenzene, derivatives thereof, and combinations thereof. Selection of the components (e.g., the organic solvent) of the kinetic hydrate inhibitor formulation may be influenced by the components of the corrosion inhibitor formulation that will be present in the aqueous liquid utilized in the downhole application, particularly when the concentrations of the corrosion inhibitor formulation and/or the kinetic hydrate inhibitor formulation and/or other treatment chemistries are being monitored via optical techniques (e.g., fluorometry, light absorbance, etc.).

The kinetic hydrate inhibitor formulations comprise an alkyl substituted polyamide homopolymer. In certain embodiments, the alkyl substituted polyamide homopolymer is present in the kinetic hydrate inhibitor formulation at a concentration of from about 2 weight percent to about 10 weight percent, including from about 2 weight percent, or from about 3 weight percent, or from about 4 weight percent, or from about 5 weight percent, or from about 6 weight percent, to about 10 weight percent, or to about 9 weight percent, or to about 8 weight percent, or to about 7 weight percent. In a preferred embodiment, the alkyl substituted polyamide homopolymer is present in the kinetic hydrate inhibitor formulation at a concentration of from about 6 weight percent to about 7 weight percent.

Generally, the kinetic hydrate inhibitor formulation will be dosed into the aqueous liquid utilized in a downhole application after the corrosion inhibitor formulation has been dosed into the aqueous liquid. In certain embodiments, the kinetic hydrate inhibitor formulation is dosed into the aqueous liquid utilized in a downhole application at a corrosion inhibitor formulation ("CI")-to-kinetic hydrate inhibitor formulation ("KHI") weight ratio of from about 1:2 to about 1:50, including from about 1:2, or from about 1:4, or from about 1:6, or from about 1:8, or from about 1:10, to about 1:50, or to about 1:40, or to about 1:30, or to about 1:20, or to about 1:15. In a preferred embodiment, the CI-to-KHI weight ratio present in the treated aqueous liquid utilized in a downhole application is from about 1:10 to about 1:15, and more preferably about 1:12.

In certain embodiments, the alkyl substituted polyamide homopolymer of the kinetic hydrate inhibitor formulation has a molecular weight of from about 1,000 daltons to about 20,000 daltons, including from about 1,000 daltons, or from about 2,000 daltons, or from about 3,000 daltons, to about 20,000 daltons, or to about 18,000 daltons, or to about 15,000 daltons. In a preferred embodiment, the alkyl substituted polyamide homopolymer of the kinetic hydrate inhibitor formulation has a molecular weight of from about 3,000 daltons to about 15,000 daltons.

The kinetic hydrate inhibitor formulations comprise an alkyl substituted polyamide copolymer. In certain embodiments, the alkyl substituted polyamide copolymer is present in the kinetic hydrate inhibitor formulation at a concentration of from about 5 weight percent to about 20 weight percent, including from about 5 weight percent, or from about 7 weight percent, or from about 9 weight percent, or from about 11 weight percent, or from about 12 weight percent, to about 20 weight percent, or to about 18 weight percent, or to about 16 weight percent, or to about 14 weight percent, or to about 13 weight percent. In a preferred embodiment, the alkyl substituted polyamide copolymer is present in the kinetic hydrate inhibitor formulation at a concentration of from about 12 weight percent to about 13 weight percent.

In certain embodiments, the alkyl substituted polyamide copolymer of the kinetic hydrate inhibitor formulation has a molecular weight of from about 1,000 daltons to about 20,000 daltons, including from about 1,000 daltons, or from about 2,000 daltons, or from about 3,000 daltons, to about 20,000 daltons, or to about 18,000 daltons, or to about 15,000 daltons. In a preferred embodiment, the alkyl substituted polyamide copolymer of the kinetic hydrate inhibitor formulation has a molecular weight of from about 3,000 daltons to about 15,000 daltons.

In certain embodiments, the alkyl substituted polyamide homopolymer and the alkyl substituted polyamide copolymer are present in the kinetic hydrate inhibitor formulation at a particular weight ratio, or at a particular range of weight ratios. For example, in certain embodiments, the alkyl substituted polyamide homopolymer and the alkyl substituted polyamide copolymer are present in the kinetic hydrate inhibitor formulation at a homopolymer-to-copolymer weight ratio of from about 1:1 to about 1:5. In a preferred embodiment, the homopolymer-to-copolymer weight ratio is about 1:2.

In certain embodiments, the kinetic hydrate inhibitor formulation is capable of producing a fluorometric response at an excitation wavelength of from about 210 nm to about 830 nm, including from about 210 nm, or from about 350 nm, or from about 440 nm, or from about 480 nm, or from about 520, to about 830 nm, or to about 680 nm, or to about 600 nm, or to about 560. In a preferred embodiment, the kinetic hydrate inhibitor formulation is capable of producing a fluorometric response at an excitation wavelength of from about 520 nm to about 560 nm.

When present, the capability of producing a fluorometric response is caused by the presence of a fluorophore in the kinetic hydrate inhibitor formulation. The fluorophore may be present in any one or more of several different chemical forms, including but not limited to one or more compositions that provide function to the kinetic hydrate inhibitor formulation (i.e., one or more components, or parts thereof, of the kinetic hydrate inhibitor formulation) and one or more compositions that do not provide function to the kinetic hydrate inhibitor formulation (i.e., one or more tracers).

For example, tracers that may be present in the kinetic hydrate inhibitor formulation include, but are not limited to, one or more dyes or intermediates thereof, one or more of certain rare earth ions, and/or one or more of certain small molecules capable of producing a fluorometric response. In certain embodiments, the fluorophore is an aromatic fluorophore, which may include, but is not limited to, a dye or intermediate thereof, present in the kinetic hydrate inhibitor formulation. In a preferred embodiment, the fluorophore is a dye. In certain embodiments, the dye comprises at least one of Rhodamine and a Rhodamine derivative. In certain embodiments, the dye of the kinetic hydrate inhibitor formulation has a Rhodamine B base. In a preferred embodiment, the fluorophore present in the kinetic hydrate inhibitor formulation is C.I. Solvent Red 49.

In certain embodiments, the fluorophore is a rare earth ion present in the kinetic hydrate inhibitor formulation. In certain embodiments, the fluorophore is a small molecule fluorescent compound present in the kinetic hydrate inhibitor formulation. When utilized, a tracer is generally present in the kinetic hydrate inhibitor formulation at relatively low concentrations, e.g., from about 0.0000001 weight percent to about 1 weight percent. In a preferred embodiment, a tracer is present in the kinetic hydrate inhibitor formulation at a concentration of from about 0.00001 weight percent to about 1 weight percent.

In certain embodiments, the fluorophore is a component, or part thereof, present in the kinetic hydrate inhibitor formulation. For example, diesel fuel generally comprises several aromatic compounds that are capable of producing a fluorometric response at an excitation wavelength of from about 210 nm to about 830 nm, including from about 350 nm, or from about 440 nm, to about 600 nm, or to about 520 nm.

The kinetic hydrate inhibitor formulation may further comprise one or more of several components, for example, water, a butoxyalcohol (e.g., 2-butoxyethanol), an aldehyde (e.g., glutaraldehyde), a substituted carboxylic acid amide, a glycol ether (e.g., diethylene glycol monoethyl ether), heavy aromatic solvent naphtha, naphthalene, ethylbenzene, trimethylbenzene, and combinations thereof.

In certain embodiments of the corrosion inhibitor formulations and the kinetic hydrate inhibitor formulations disclosed herein (together "the formulations"), each respective formulation is capable of utilization at temperatures of from about 0° C. to about 100° C.

In making the corrosion inhibitor formulations and kinetic inhibitor formulations disclosed herein, any of several methods may be utilized as known in the art to mix the several components and other ingredients, including, for example, batch mixing, continuous mixing, in-line mixing, the like, and combinations thereof. The formulations may be created and stored for later use, or the formulations may be created as needed and dosed directly to the downhole application.

At a minimum, when present and intended for utilization in a method that includes fluorometric techniques, the fluorophore is present in the corrosion inhibitor formulation and/or the kinetic hydrate inhibitor formulation at a known ratio of fluorophore-to-corrosion inhibitor and/or fluorophore-to-kinetic hydrate inhibitor. For example, one practicing the methods discussed herein may choose to fluorometrically monitor and/or control the dosing of either the corrosion inhibitor formulation or the kinetic hydrate inhibitor formulation, or both.

In a preferred embodiment, a fluorophore is present the corrosion inhibitor formulation and/or the kinetic hydrate inhibitor formulation at a known ratio with one or more active ingredient(s) of each respective formulation. For example, a corrosion inhibitor formulation may comprise an alkyl pyridine quaternary ammonium salt, a phosphate ester, and diesel fuel (a component having parts that are capable of producing a fluorometric response at an excitation wavelength of from about 210 nm to about 830 nm). In a preferred embodiment, the organic solvent (e.g., diesel fuel) is present in the corrosion inhibitor formulation at a known ratio with at least one of the alkyl pyridine quaternary ammonium salt and the phosphate ester. For example, the known ratio may be 1 part by weight diesel fuel per 2 parts by weight alkyl pyridine quaternary ammonium salt, or 1 part by weight diesel fuel per 1 part by weight phosphate ester, or 1 part by weight diesel fuel per 3 parts by weight alkyl pyridine quaternary ammonium salt and phosphate ester.

In certain embodiments of the formulations set forth herein, two or more components are present in a mixture prior to the respective formulation and the mixture is combined with the other components of the respective formulation to arrive at the final formulation. For example, the ethoxylated fatty amine, the imidazoline, and the benzyl alkyl pyridinium salt may be present as a mixture separate from the other components of the corrosion inhibitor formulation, and the mixture may be combined with the other components and any fluorophore(s) to arrive at the corrosion inhibitor formulation.

Methods of treating an aqueous liquid utilized in a downhole application are provided. In an embodiment, the method comprises dosing a kinetic hydrate inhibitor formulation at a kinetic hydrate inhibitor dosage rate into the aqueous liquid utilized in the downhole application. The aqueous liquid comprises water, a surfactant (e.g., an ethoxylated fatty amine), an organic solvent, and at least one of an alkyl pyridine quaternary ammonium salt and a phosphate ester. The kinetic hydrate inhibitor formulation comprises an alkyl substituted polyamide homopolymer and an alkyl substituted polyamide copolymer. In certain embodiments, the organic solvent comprises at least one of a mono-ring aromatic compound, a di-ring aromatic compound, and a tri-ring aromatic compound, derivatives thereof, and combinations thereof. In certain embodiments, the organic solvent is diesel fuel. The kinetic hydrate inhibitor may further comprise a fluorophore.

In an embodiment, the method of treating an aqueous liquid utilized in a downhole application comprises dosing a corrosion inhibitor formulation at a corrosion inhibitor dosage rate into the aqueous liquid utilized in the downhole application. The corrosion inhibitor formulation comprises an active ingredient and an organic solvent, the corrosion inhibitor formulation being capable of providing a fluorometric response proportional to the concentration of the dosed corrosion inhibitor formulation, or active ingredient thereof, when present in the aqueous liquid utilized in the downhole application. A fluorometric response proportional to the concentration of the dosed corrosion inhibitor formulation, or active ingredient thereof, present in the aqueous liquid containing the dosed corrosion inhibitor formulation is created and measured. The corrosion inhibitor dosage rate into the aqueous liquid is adjusted based on the created and measured fluorometric response. The method may further comprise dosing a kinetic hydrate inhibitor formulation at a kinetic hydrate inhibitor dosage rate into the aqueous liquid utilized in the downhole application.

In an embodiment, the method of treating an aqueous liquid utilized in a downhole application comprises dosing a corrosion inhibitor formulation at a corrosion inhibitor dosage rate into the aqueous liquid utilized in the downhole application. A kinetic hydrate inhibitor formulation is dosed into the aqueous liquid utilized in the downhole application at a kinetic hydrate inhibitor dosage rate. The kinetic hydrate inhibitor formulation comprises an active ingredient, an organic solvent, and a tracer at a known ratio with the active ingredient and capable of providing a fluorometric response proportional to the concentration of the dosed kinetic hydrate inhibitor formulation, or active ingredient thereof, when present in the aqueous liquid utilized in the downhole application. A fluorometric response proportional to the concentration of the dosed kinetic hydrate inhibitor formulation, or active ingredient thereof, present in the aqueous liquid containing the dosed corrosion inhibitor and kinetic hydrate inhibitor formulations is created and measured. The kinetic hydrate inhibitor dosage rate is adjusted based on the created and measured fluorometric response.

A method of controlling dosage of corrosion inhibitor into an aqueous liquid utilized in a downhole application is provided. The method comprises dosing a corrosion inhibitor formulation at a corrosion inhibitor dosage rate into the aqueous liquid utilized in the downhole application. The corrosion inhibitor formulation comprises an active ingredient and an organic solvent. The corrosion inhibitor formulation is capable of providing a fluorometric response proportional to the concentration of the dosed corrosion inhibitor formulation, or active ingredient thereof, when present in the aqueous liquid utilized in the downhole application. Light having a wavelength of from about 210 nm to about 830 nm is shone into the aqueous liquid containing the corrosion inhibitor formulation, thereby causing a fluorometric emission at a wavelength of from about 230 nm to about 850 nm. The fluorometric emission at the wavelength of from about 230 nm to about 850 nm is detected. The corrosion inhibitor dosage rate into the aqueous liquid is adjusted based on the detected fluorometric emission at the wavelength of from about 230 nm to about 850 nm.

A method of controlling dosage of kinetic hydrate inhibitor into an aqueous liquid utilized in a downhole application is provided. The phrase "an aqueous liquid utilized in a downhole application" is used to describe a liquid comprising water that is being used, has been used, or will be used to aid in the extraction of a fluid hydrocarbon substance, e.g., a fluid fossil fuel. For example, an aqueous liquid utilized in a downhole application may be used to aid in the extraction of at least one of natural gas and crude oil. The term "liquid" is used to describe a substance that comprises a liquid, which includes, but is not limited to, liquids, liquid solutions, slurries, emulsions, dispersions, and the like. In a preferred embodiment, the downhole application is a natural gas well that is substantially free of liquid hydrocarbons.

The method comprises dosing a corrosion inhibitor formulation at a corrosion inhibitor dosage rate into the aqueous liquid utilized in the downhole application. A kinetic hydrate inhibitor formulation is dosed at a kinetic hydrate inhibitor dosage rate into the aqueous liquid utilized in the downhole application. The kinetic hydrate inhibitor formulation comprises an active ingredient, an organic solvent, and a tracer at a known proportion with the active ingredient. The kinetic hydrate inhibitor formulation is capable of providing a fluorometric response proportional to the concentration of the dosed kinetic hydrate inhibitor formulation, or active ingredient thereof, when present in the aqueous liquid utilized in the downhole application. Light having a wavelength of from about 210 nm to about 830 nm is shone into the aqueous liquid containing the corrosion inhibitor and kinetic hydrate inhibitor formulations, thereby causing a fluorometric emission at a wavelength of from about 230 nm to about 850 nm. The fluorometric emission at the wavelength of from about 230 nm to about 850 nm is detected. The kinetic hydrate inhibitor dosage rate into the aqueous liquid is adjusted based on the detected fluorometric emission at the wavelength of from about 230 nm to about 850 nm.

In certain embodiments, the aqueous liquid utilized in a downhole application has a turbidity of from about 0 NTU to about 130,000 NTU, including from about 0 NTU, or from about 100 NTU, or from about 500 NTU, or from about 1,000 NTU, to about 100,000 NTU, or to about 85,000 NTU, or to about 50,000 NTU, or to about 20,000 NTU, or to about 10,000 NTU, or to about 5,000 NTU. In a preferred embodiment, the aqueous liquid utilized in a downhole application has a turbidity of from about 100 NTU to about 5,000 NTU.

Fluorometric techniques generally require reasonably clear substances in order to accurately detect fluorescence, and consequently certain concentration measurements, of a particular substance. However, for the methods disclosed herein, the aqueous liquid utilized in a downhole application may be relatively light-absorbing, e.g., has a high light absorbance value. In certain embodiments, the aqueous liquid utilized in a downhole application has a light absorbance of from about 0 absorbance units, including from about 0.4 absorbance units, or from about 1 absorbance units, to about 1,500 absorbance units, or to about 1,000 absorbance units, or to about 400 absorbance units, or to about 100 absorbance units, or to about 50 absorbance units, or to about 20 absorbance units, or to about 10 absorbance units, or to about 5 absorbance units. In a preferred embodiment, the aqueous liquid utilized in a downhole application has a light absorbance of from about 0.4 absorbance units to about 5 absorbance units.

Light absorbance units are described in the Background section herein, in relation to absorbance units combined total for excitation and emission lightpaths when using a 1 cm pathlength cell. Furthermore, when a corrosion inhibitor formulation and a kinetic hydrate inhibitor formulation are dosed into relatively clean water, the formulations have a tendency to create a relatively turbid mixture (e.g., having a turbidity of from about 50 NTU to about 130,000 NTU), regardless of the existence of turbidity in the water prior to the mixing of the formulations.

Treated aqueous liquids that exhibit high light absorbance (e.g., having turbidity greater than a threshold value) can be diluted with, e.g., water in order to provide a sample of the treated aqueous liquid that may be suitably tested via the fluorometric methods disclosed herein. For example, a volume (e.g., 1 volume) of treated aqueous liquid having turbidity greater than a threshold value may be diluted with a known volume (e.g., 9 volumes) of water, resulting in a sample that is less turbid and capable of turbidity measurement via, e.g., light scattering techniques. The turbidity of the diluted sample is then measured, resulting in a measurement of, e.g., 30 NTU. The dilution factor was 1 volume of original sample to 10 volumes of diluted sample. The measured value is multiplied by 10 to reach the turbidity value of the original sample, i.e., 300 NTU. Similar dilution and calculation can be done for light absorbance measurements, which explains why values of, for example, 1500 absorbance units (and, for example, 130,000 NTU turbidity values) can be obtained using the dilution method set forth.

The term "active ingredient" refers to one or more components of a formulation, excluding any solvent and water. For example, for a corrosion inhibitor formulation comprising an alkyl pyridine quaternary ammonium salt, a phosphate ester and diesel fuel, the active ingredient can be any one or combination of components that are not solvents, i.e., not diesel fuel. Other solvents may be present as well. For the preferred corrosion inhibitor formulations presented herein, alkyl pyridine quaternary ammonium salt, phosphate ester, ethoxylated fatty amine, benzyl imidazolinium salt, and benzyl alkyl pyridinium salt are each active ingredients, though utilization of the term "active ingredient" is not limited to any one or combination of these exemplary active ingredients of a corrosion inhibitor formulation. For the preferred kinetic hydrate inhibitor formulations presented herein, alkyl substituted polyamide and alkyl substituted alkyl polyamide copolymer are each active ingredients, though utilization of the term "active ingredient" is not limited to any one or combination of these exemplary active ingredients of a kinetic hydrate inhibitor formulation.

Generally, the corrosion inhibitor formulation is dosed into the aqueous liquid utilized in the downhole application prior to, upon, or shortly after entering the downhole application. Generally, the corrosion inhibitor is dosed at the well head platform(s), prior to the aqueous liquid entering the downhole application, and generally under turbulent conditions. In certain embodiments, the corrosion inhibitor formulation is dosed into the aqueous liquid at a temperature of from about 50° C. to about 80° C.

Preferably, the kinetic hydrate inhibitor formulation, when dosed into an aqueous liquid utilized in a downhole application, is dosed after the dosing of a corrosion inhibitor formulation. In other words, preferably, the corrosion inhibitor formulation will be present in the aqueous liquid utilized in the downhole application at the time and location that the kinetic hydrate inhibitor formulation is dosed into the aqueous liquid utilized in the downhole application. The kinetic hydrate inhibitor formulation is dosed at the tie-in platform, e.g., prior to the treated aqueous liquid traveling through a single trunk line to, e.g., a gas plant. In certain embodiments, the kinetic hydrate inhibitor formulation is dosed into the aqueous liquid at a temperature of from about 10° C. to about 60° C.

The corrosion inhibitor formulations of the present disclosure may be dosed into an aqueous liquid. The aqueous liquid may be utilized in at least one of a downhole application, a top side application, and a subsea wellhead. Furthermore, the aqueous liquid may be utilized in a top side application after having been utilized in a downhole application. In other words, the phrase "an aqueous liquid utilized in a downhole application" includes, e.g., aqueous liquids that will be utilized in a downhole application, aqueous liquids that are being utilized in a downhole application, and aqueous liquids that have been utilized in a downhole application, and combinations thereof. In a preferred embodiment, the corrosion inhibitor formulation is dosed into the aqueous liquid utilized in a downhole application at a top side application, which in certain embodiments is a wellhead platform. In a preferred embodiment, the kinetic hydrate inhibitor formulation is dosed into the aqueous liquid utilized in a downhole application in at least one of a tie-in platform and a subsea wellhead.

The corrosion inhibitor formulations of the present disclosure may be dosed into an aqueous liquid utilized in a downhole application at a constant dosage rate or a variable dosage rate. The corrosion inhibitor formulations may be dosed continuously or intermittently. Generally, corrosion inhibitor formulations may be dosed into an aqueous liquid utilized in a downhole application at a rate of from about 100 mg to about 100,000 mg per liter of aqueous liquid, including from about 100 mg, or from about 500 mg, or from about 1,000 mg, to about 100,000 mg, or to about 50,000 mg, or to about 20,000 mg, or to about 10,000 mg, or to about 5,000 mg, or to about 2,000 mg, per liter of aqueous liquid. In a preferred embodiment, the corrosion inhibitor formulation is dosed into an aqueous liquid utilized in a downhole application at a rate of from about 1,000 mg to about 2,000 mg per liter of aqueous liquid, and more preferably at a rate of about 1,500 mg per liter of aqueous liquid.

Generally, the kinetic hydrate inhibitor formulations of the present disclosure will be utilized in certain types of downhole applications. A kinetic hydrate inhibitor is generally necessary when the downhole application involves off-shore applications. When utilized, the kinetic hydrate inhibitor formulations of the present disclosure may be dosed into an aqueous liquid utilized in a downhole application at a constant dosage rate or a variable dosage rate. The kinetic hydrate inhibitor formulations, when utilized, may be dosed continuously or intermittently. Generally, when utilized, kinetic hydrate inhibitor formulations may be dosed into an aqueous liquid utilized in a downhole application at a rate of from about 1,000 mg to about 100,000 mg per liter of aqueous liquid, including from about 1,000 mg, or from about 5,000 mg, or from about 10,000 mg, to about 100,000 mg, or to about 50,000 mg, or to about 30,000 mg per liter of aqueous liquid. In a preferred embodiment, the kinetic hydrate inhibitor formulation is dosed into an aqueous liquid utilized in a downhole application at a rate of from about 10,000 mg to about 30,000 mg per liter of aqueous liquid, and more preferably at a rate of about 20,000 mg per liter of aqueous liquid.

In certain embodiments, the method of treating an aqueous liquid utilized in a downhole application comprises, inter alia, creating and measuring a fluorometric response proportional to the concentration of the dosed corrosion inhibitor and/or kinetic hydrate inhibitor formulation, or active ingredient(s) thereof, present in the aqueous liquid containing the dosed corrosion inhibitor formulation and/or kinetic hydrate inhibitor formulation, i.e., creating a fluorometric response. A preferred method of creating and measuring a fluorometric response is carried out by shining light at a certain excitation wavelength, or range thereof, into the aqueous liquid containing the corrosion inhibitor formulation and/or the kinetic hydrate inhibitor formulation, thereby causing a fluorometric emission at a certain emission wavelength, or range thereof, and detecting the fluorometric emission at the certain emission wavelength.

In conducting the methods that include fluorometric techniques, the fluorometric techniques may be conducted using a light source and a fluorescence detector (e.g., fluorometer) configured to fluorometrically detect fluorescence in a liquid as known in the art. In a preferred embodiment, the fluorometric techniques are carried out using a light source capable of shining light at a particular wavelength, or range thereof, into an aqueous liquid utilized in a downhole application that has been treated with a corrosion inhibitor formulation and optionally a kinetic hydrate inhibitor formulation.

In a preferred embodiment, the treated aqueous liquid utilized in a downhole application is present in a flow cell, which is preferably a cylindrical flow cell. The fluorescence detector is configured to detect fluorometric emission from the treated aqueous liquid utilized in a downhole application. In a preferred embodiment, the detecting is performed by a fluorescence detector located at an angle of from about 10 degrees to about 120 degrees from the light being shone into a cylindrical flow cell containing the aqueous liquid, the corrosion inhibitor formulation and optionally the kinetic hydrate inhibitor formulation. In a further preferred embodiment, the detecting is performed by a fluorescence detector located at an angle of from about 85 degrees to about 95 degrees from the light being shone into a cylindrical flow cell containing the aqueous liquid, the corrosion inhibitor formulation and optionally the kinetic hydrate inhibitor formulation. While not wishing to be bound by theory, the fluorometric response is believed to be created at the surface of the aqueous liquid utilized in the downhole application and travels along the edge of the flow cell.

As is apparent, a plurality of apparatuses (e.g., light source, fluorescence detector, and/or flow cell) and/or systems (e.g., a combination of certain apparatuses) for performing fluorometric techniques may be utilized to measure the fluorometric responses of each of the corrosion inhibitor formulation and the kinetic hydrate inhibitor formulation. Apparatuses and systems capable of carrying out the methods of the present disclosure are available, for example, from Nalco Champion, 3200 Southwest Freeway, Suite 2700, Houston, Tex. 77027.

In a preferred embodiment, fluorometric response is achieved and measured using a multi-channel LED light source fluorometer, with each optical board of the fluorometer has one LED and three photodiode (i.e., fluorescence) detectors (one detector each measuring fluorescence, LED intensity through the sample cell, and turbidity, respectively). In this particular preferred embodiment, the fluorometer is configured to perform measurements (e.g., "creating and measuring fluorometric response" and "shining light at a wavelength . . . ; detecting the fluorometric emission") of the treated aqueous liquid via a quartz tube sample flow cell having a diameter of 0.6 cm. In this particular preferred embodiment, the photodiode that measures LED intensity is located about 180 degrees from the excitation light source (e.g., an LED light source or xenon arc lamp). In this particular preferred embodiment, the detectors that measure fluorescence and turbidity are located at about 90 degrees and about 270 degrees from the excitation light source. An additional photodiode detector may be optionally located near the excitation light source, which may provide information related to treated aqueous liquids having exceptionally high light absorbance (e.g., greater than 400 absorbance units).

The multi-channel LED light source fluorometer is adapted to provide excitation light at certain wavelengths, and adapted to detect fluorometric emission (i.e., fluorometric response) at certain emission wavelengths that correspond to the presence and concentration of fluorophores dosed into the treated aqueous liquid. In preferred embodiments, the multi-channel LED light source fluorometer is outfitted with optical filters to achieve the creating and measuring of the fluorometric response, and the shining and detecting.

The following examples further illustrate the invention but, of course, should not be construed as in any way limiting its scope. For the examples presented herein, a Hitachi F-7000 dual monochromator scanning fluorescence spectrophotometer with a xenon arc lamp source and 1 cm diameter quartz sample cuvette was utilized to conduct light-related measurements (e.g., fluorometric excitation and emission detection).

Example 1

Generally, the impact of relatively high light absorbance (e.g., from about 0.4 absorbance units to about 1,500 absorbance units) on fluorometric response prohibits the accurate use of fluorometric techniques to measure the presence (or absence) and/or concentration of a fluorophore in such a liquid (e.g., an aqueous liquid). Particularly, the complexity of the impact of light absorbance on fluorometric response becomes even greater when light absorbance at excitation and emission wavelengths are not equal and/or absorbance does not increase linearly as dosage of the light absorbing substance increases. While not wishing to be bound by theory, the impact of light absorbance on fluorometric response occurs whether light absorbance arises from contaminants (e.g., sample turbidity) in the sample being analyzed, from the treatment chemistry (e.g., the corrosion inhibitor formulation and/or the kinetic hydrate inhibitor formulation) being dosed, or both.

FIG. 1 is a plot of data related to light absorbance that occurs at various wavelengths of light shone into a sample of aqueous liquid comprising a corrosion inhibitor formulation and a kinetic hydrate inhibitor formulation as described herein (i.e., a treated aqueous liquid), wherein the corrosion inhibitor formulation ("CI") and the kinetic hydrate inhibitor formulation ("KHI") are present at a CI-to-KHI weight ratio of about 1:12. The various treated aqueous liquids had light absorbance as shown in FIG. 1, and turbidity values ranging from 2,000 NTU to 10,000 NTU. The corrosion inhibitor formulation comprised 25 weight percent alkyl pyridine quaternary ammonium chloride, 12.5 weight percent phosphate ester, about 3.5 weight percent ethoxylated tallow amine, about 3.5 weight percent benzyl imidazolinium chloride, about 3.5 weight percent benzyl alkyl pyridinium chloride, 12.5 weight percent diesel fuel, 24.25 weight percent ethoxybutanol, 7 weight percent 2-mercaptoethanol, and 7.5 weight percent ethylene glycol. The corrosion inhibitor formulation was present in the aqueous liquid at concentrations ranging from 0 mg/L of sample to 24 g/L of sample. The kinetic hydrate inhibitor formulation was formulated as described herein, comprising an alkyl substituted polyamide homopolymer and an alkyl substituted polyamide copolymer at an alkyl substituted polyamide homopolymer-to-alkyl substituted polyamide copolymer weight ratio of about 1:2, and further comprising 2-butoxyethanol, diethylene glycol monoethyl ether, heavy aromatic naphtha, naphthalene, less than 1 weight percent each of water, glutaraldehyde, substituted carboxylic acid amide, ethylbenzene, 1,2,4-trimethylbenzene, and 0.00003 weight percent C.I. Solvent Red 49. The kinetic hydrate inhibitor formulation was present in the aqueous liquid at concentrations ranging from 0 mg/L of sample to 24 g/L of sample.

Given the non-linear and significant light absorbance of the sample, as illustrated in FIG. 1, a fluorometric response would not be predictable, or even expected, from the sample that would be proportional to the concentration of either formulation, or active ingredient(s) thereof, particularly from traditional fluorometric techniques (e.g., using a light source, cylindrical flow cell, and fluorescence detector, wherein the fluorescence detector is located at an angle of from about 10 degrees to about 120 degrees, or from about 85 degrees to about 95 degrees, and in this case, about 90 degrees, from the light being shone into a cylindrical flow cell containing the aqueous liquid).

Example 2

FIG. 2 is a plot of experimental data related to fluorometric testing of the sample described in Example 1 using traditional fluorometric techniques as described herein with varying concentrations of kinetic hydrate inhibitor formulation. Given the non-linear and significant light absorbance as described, Equation 1 predicts a fluorometric response related to the concentration of the kinetic hydrate inhibitor formulation at an excitation wavelength of 532 nm. However, the actual fluorometric response related to the concentration of the kinetic hydrate inhibitor formulation at an excitation wavelength of 532 nm was measured and is plotted, which was surprising in light of the expected fluorometric response. Particularly, at kinetic hydrate inhibitor formulation concentrations of from about 1 g/L to about 24 g/L of sample (i.e., treated aqueous liquid), the fluorometric response increased in a relatively linear manner, which was unexpected. The emission wavelength at an excitation of 532 nm for the given kinetic hydrate inhibitor formulation was 634 nm.

Example 3

FIG. 3a is a plot of experimental data related to fluorometric testing of the sample described in Examples 1 and 2 using traditional fluorometric techniques as described herein. For the given sample, as shown in FIG. 3a, the actual fluorometric response related to the concentration of corrosion inhibitor formulation present in the aqueous liquid at an excitation wavelength of 365 nm (i.e., at an excitation wavelength that provides the maximum, or at least nearly the maximum, fluorometric response for the fluorophores found in diesel fuel) was measured and is plotted. As is demonstrated from the plotted data of FIG. 3a, the response was inversely proportional to the concentration of the corrosion inhibitor formulation present in the sample. The results demonstrate the unpredictable nature of using traditional fluorometric techniques to measure fluorometric response in aqueous liquids having relatively high light absorption (e.g., aqueous liquids utilized in downhole applications and/or aqueous liquids treated with both a corrosion inhibitor formulation and a kinetic hydrate inhibitor formulation). The emission wavelength at an excitation of 365 nm for the given corrosion inhibitor formulation was 405 nm.

FIG. 3b is a plot of experimental data related to fluorometric testing of the sample described above and in Examples 1 and 2 using traditional fluorometric techniques as described herein. Given the inverse dependency shown in FIG. 3a believed to be caused at least in part by the non-linear and significant light absorbance as described, Equation 1 predicts a fluorometric response related to the concentration of the corrosion inhibitor formulation at an excitation wavelength of 465 nm (i.e., at an excitation wavelength that provides from 20 to 60 percent of the maximum fluorometric response for the fluorophore(s) found in the corrosion inhibitor formulation, e.g., fluorophores found in diesel fuel). However, the actual fluorometric response related to the concentration of the corrosion inhibitor formulation at an excitation wavelength of 465 nm was measured and is plotted. Particularly, at corrosion inhibitor formulation concentrations of from about 100 mg/L to about 2 g/L of aqueous liquid, the fluorometric response increased in a relatively linear manner, which was unexpected, which was surprising in light of the expected fluorometric response and the inverse dependency at 365 nm. The emission wavelength at an excitation of 465 nm for the given corrosion inhibitor formulation was 538 nm.

Example 4

FIG. 4 is a plot of experimental data demonstrating dosing the corrosion inhibitor formulation and the kinetic hydrate inhibitor formulation of Examples 1-3 into an aqueous liquid at known concentrations, followed by creating and measuring a fluorometric response proportional to the concentration of the dosed corrosion inhibitor formulation when the kinetic hydrate inhibitor formulation includes a tracer. FIG. 4 demonstrates consistent results related to the concentration of the corrosion inhibitor formulation, or active ingredient(s) thereof, present in the aqueous liquid as measured using traditional fluorometric techniques as described herein. The fluorometric response of the fluorophore of the corrosion inhibitor formulation was created and measured via traditional fluorometric techniques at an excitation wavelength of 465 nm, and an emission wavelength of 538 nm. Given the results of Example 2, the concentration of the kinetic hydrate inhibitor formulation can be obtained via traditional fluorometric techniques using a tracer or component capable of providing a fluorometric response proportional to the concentration of the dosed kinetic hydrate inhibitor formulation and without interfering with the excitation and emission wavelengths of the fluorometric measurement of the concentration of the corrosion inhibitor formulation. For the given examples, the kinetic hydrate inhibitor formulation having a Rhodamine B based tracer provides a fluorophore that fits the aforementioned requirements, capable of excitation at a wavelength of 532 nm with an emission wavelength of 634 nm. The trend demonstrated in FIG. 4 was also obtained for the kinetic hydrate inhibitor formulation present in the sample having a kinetic hydrate inhibitor formulation concentration of 17.5 g/L using traditional fluorometric techniques and a Rhodamine B based tracer (excitation wavelength of 532 nm and emission wavelength of 634 nm).

The Examples provide evidence that the formulations and methods described herein are broadly applicable to determining fluorometric response, and consequently certain chemical concentrations, in aqueous liquids having relatively high and/or non-linear light absorbance (e.g., highly turbid aqueous liquids), more particularly applicable to determining fluorometric response, and consequently concentration, in an aqueous liquid, such as, e.g., an aqueous liquid utilized in a downhole application, wherein the aqueous liquid comprises at least one of a corrosion inhibitor formulation and a kinetic hydrate inhibitor formulation, and particularly wherein the aqueous liquid comprises both a corrosion inhibitor formulation and a kinetic hydrate inhibitor formulation.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A method of treating an aqueous liquid utilized in a downhole application, the method comprising: dosing a corrosion inhibitor formulation at a corrosion inhibitor dosage rate into the aqueous liquid utilized in the downhole application;
dosing a kinetic hydrate inhibitor formulation at a kinetic hydrate inhibitor dosage rate into the aqueous liquid utilized in the downhole application, the kinetic hydrate inhibitor formulation comprising an active ingredient, an organic solvent, and a tracer at a known ratio with the active ingredient and capable of providing a fluorometric response proportional to the concentration of the dosed kinetic hydrate inhibitor formulation, or active ingredient thereof, when present in the aqueous liquid utilized in the downhole application;
wherein the kinetic hydrate inhibitor formulation is dosed such that the concentration of the kinetic hydrate inhibitor is in a range of 1 g/L to 24 g/L of the aqueous liquid being treated, and wherein the active ingredient comprises an alkyl substituted polyamide homopolymer and an alkyl substituted polyamide copolymer;
creating and measuring a fluorometric response proportional to the concentration of the dosed kinetic hydrate inhibitor formulation, or active ingredient thereof, present in the aqueous liquid containing the dosed corrosion inhibitor and kinetic hydrate inhibitor formulations;
wherein the fluorometric response is produced by exciting at a wavelength in the range of 440 nm to 600 nm and measuring the fluorometric response at a higher wavelength in the range of 520 nm to 634 nm;
adjusting the kinetic hydrate inhibitor dosage rate into the aqueous liquid based on the created and measured fluorometric response;
wherein the aqueous liquid has a light absorbance of from about 0.4 absorbance units to about 1,500 absorbance units.

2. The method of claim 1, wherein the aqueous liquid has a turbidity of from about 50 NTU to about 130,000 NTU.

3. The method of claim 1, wherein the measuring the fluorometric response is performed via traditional fluorometric techniques.

4. The method of claim 1, wherein the measuring the fluorometric response is performed utilizing a cylindrical flow cell.

5. The method of claim 4, wherein the measuring the fluorometric response is performed utilizing a fluorescence detector located at an angle of from about 10 degrees to about 120 degrees from light shone into the cylindrical flow cell containing the aqueous liquid and the corrosion inhibitor formulation.

6. The method of claim 4, wherein the measuring the fluorometric response is performed utilizing a fluorescence detector located at an angle of from about 85 degrees to about 95 degrees from light shone into the cylindrical flow cell containing the aqueous liquid and the corrosion inhibitor formulation.

7. The method of claim 1, wherein the tracer is C.I. Solvent Red 49.

8. A method of controlling dosage of kinetic hydrate inhibitor into an aqueous liquid utilized in a downhole application, the method comprising:
dosing a corrosion inhibitor formulation at a corrosion inhibitor dosage rate into the aqueous liquid utilized in the downhole application;
dosing a kinetic hydrate inhibitor formulation at a kinetic hydrate inhibitor dosage rate into the aqueous liquid utilized in the downhole application, the kinetic hydrate inhibitor formulation comprising an active ingredient, an organic solvent, and a tracer at a known ratio with the active ingredient, wherein the kinetic hydrate inhibitor formulation is capable of providing a fluorometric response proportional to the concentration of dosed kinetic hydrate inhibitor formulation, or active ingredient thereof, when present in the aqueous liquid utilized in the downhole application;
wherein the kinetic hydrate inhibitor formulation is dosed such that the concentration of the kinetic hydrate inhibitor is in a range of 1 g/L to 24 g/L of the aqueous liquid being treated and wherein the active ingredient of the kinetic hydrate inhibitor formulation comprises at least one of an alkyl substituted polyamide homopolymer and an alkyl substituted polyamide copolymer;
shining light at a wavelength of from 440 nm to 600 nm into the aqueous liquid containing the corrosion inhibitor and kinetic hydrate inhibitor formulations, thereby causing a fluorometric emission at a higher wavelength of from 520 nm to 634 nm;
detecting the fluorometric emission;
adjusting the kinetic hydrate inhibitor dosage rate into the aqueous liquid based on the detected fluorometric emission;
wherein the aqueous liquid has a light absorbance of from about 0.4 absorbance units to about 1,500 absorbance units.

9. The method of claim 8, wherein the light is shone into the aqueous liquid containing the corrosion inhibitor and kinetic hydrate inhibitor formulations at a wavelength of from about 520 nm to about 600 nm.

10. The method of claim 8, wherein the aqueous liquid has a turbidity of from about 50 NTU to about 130,000 NTU.

11. The method of claim 8, wherein the fluorometric detecting is performed via traditional fluorometric techniques.

12. The method of claim 8, wherein the fluorometric detecting is performed utilizing a cylindrical flow cell.

13. The method of claim 12, wherein the fluorometric detecting is performed by a fluorescence detector located at an angle of from about 10 degrees to about 120 degrees from the light shone into the cylindrical flow cell containing the aqueous liquid, the corrosion inhibitor formulation, and the kinetic hydrate inhibitor formulation.

14. The method of claim 12, wherein the fluorometric detecting is performed by a fluorescence detector located at an angle of from about 85 degrees to about 95 degrees from the light shone into the cylindrical flow cell containing the aqueous liquid, the corrosion inhibitor formulation, and the kinetic hydrate inhibitor formulation.

15. The method of claim 8, wherein the tracer comprises a dye or intermediate thereof.

16. The method of claim 15, wherein the dye or intermediate thereof comprises at least one of Rhodamine and a Rhodamine derivative.

17. The method of claim 8, wherein the tracer is C.I. Solvent Red 49.

* * * * *

UNITED STATES PATENT AND TRADEMARK OFFICE
CERTIFICATE OF CORRECTION

PATENT NO. : 10,466,175 B2  
APPLICATION NO. : 15/018281  
DATED : November 5, 2019  
INVENTOR(S) : Abla et al.

Page 1 of 1

It is certified that error appears in the above-identified patent and that said Letters Patent is hereby corrected as shown below:

In the Claims

At Column 22, Claim 8, Line 19, delete "being treated and wherein" and insert --being treated, and wherein--

Signed and Sealed this  
Eleventh Day of February, 2020

Andrei Iancu  
*Director of the United States Patent and Trademark Office*